(12) United States Patent
Goshen

(10) Patent No.: US 9,247,919 B2
(45) Date of Patent: Feb. 2, 2016

(54) METHOD AND SYSTEM FOR DUAL ENERGY CT IMAGE RECONSTRUCTION

(75) Inventor: Liran Goshen, Pardes-Hanna (IL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 148 days.

(21) Appl. No.: 13/982,275

(22) PCT Filed: Jan. 18, 2012

(86) PCT No.: PCT/IB2012/050234
§ 371 (c)(1),
(2), (4) Date: Jul. 29, 2013

(87) PCT Pub. No.: WO2012/104740
PCT Pub. Date: Aug. 9, 2012

(65) Prior Publication Data
US 2013/0308745 A1    Nov. 21, 2013

Related U.S. Application Data

(60) Provisional application No. 61/438,344, filed on Feb. 1, 2011.

(51) Int. Cl.
*A61B 6/00* (2006.01)
*G06T 11/00* (2006.01)

(52) U.S. Cl.
CPC .................. *A61B 6/52* (2013.01); *G06T 11/005* (2013.01); *G06T 2211/408* (2013.01)

(58) Field of Classification Search
CPC .......... A61B 6/032; A61B 6/52; A61B 6/482; G06T 2211/408; G06T 11/005; G01N 23/046
USPC .................................................. 378/4, 5, 901
See application file for complete search history.

(56) References Cited

U.S. PATENT DOCUMENTS

| | | |
|---|---|---|
| 2004/0102688 A1 | 5/2004 | Walker et al. |
| 2009/0092219 A1 | 4/2009 | Wu et al. |
| 2009/0097611 A1 | 4/2009 | Nishide et al. |
| 2009/0116722 A1 | 5/2009 | Chen et al. |

(Continued)

FOREIGN PATENT DOCUMENTS

WO    2012073140 A1    6/2012

OTHER PUBLICATIONS

Bertram, M., et al.; Directional Interpolation of sparsely sampled cone-beam CT sinogram data; 2004; Proceedings IEEE Int'l Symposium on Biomedical Imaging; vol. 1:928-931.

(Continued)

*Primary Examiner* — Jurie Yun

(57) ABSTRACT

A method and system for dual energy CT image reconstruction are provided. In one aspect, a fast kVp switching x-ray source is used during an imaging scan to produce a low energy x-ray beam for L consecutive projection angles, and then to produce a high energy x-ray beam for H consecutive projection angles, wherein L is substantially less than H. Various methods are provided for estimating the resulting undersampled data in the low energy projection data set and the high energy projection data set. The missing low energy projection data may be estimated from the known high energy projection data using any one of several disclosed structural propagation embodiments.

25 Claims, 4 Drawing Sheets

(56) References Cited

U.S. PATENT DOCUMENTS

2010/0189212 A1 7/2010 Zou
2010/0215233 A1 8/2010 Hsieh

OTHER PUBLICATIONS

Bertram, M., et al.; Directional View Interpolation for Compensation of Sparse Angular Sampling in Cone-Beam CT; 2009; IEEE Trans. on Medical Imaging; 28(7)1011-1022.

Carmi, R., et al.; A unique noncathartic CT colonography approach by using two-layer dual-energy MDCT and a special algorithmic colon cleansing method; 2008; Nuclear Science Symposium Conf. Record; pp. 4780-4783.

Comaniciu, D., et al.; Mean Shift: A robust Approach toward Feature Space Analysis; 2002; IEEE Trans. on Pattern Analysis and Machine Intelligence; 24(5)603-619.

Grevera, G. J., et al.; An objective comparison of 3-D image interpolation methods; 1998; IEEE Trans. on Medical Imaging; 17(4)642-652.

Hladuvka, J., et al.; Direction-Driven Shape-Based Interpolation of Volume Data; 2001; Proceedings Vision, Modeling and Visualization, Stuttgart, Germany; pp. 113-120 and 521.

Huh, W., et al.; Model-Based Image Reconstruction for Dual-energy X-Ray CT with Fast KVP Switching; 2009; IEEE; pp. 326-329.

Lehmann, T. M., et al.; Survey: Interpolation Methods in Medical Image Processing; 1999; IEEE Trans on Medical Imaging; 18(11)1049-1075.

Lehmann, T. M., et al.; Addendum: B-Spline Interpolation in Medical Image Processing; 2001; IEEE Trans on Medical Imaging; 20(7)660-665.

Perona, P., et al.; Scale-Space and Edge Detection Using Anisotropic Diffusion; 1990; IEEE Trans. on Pattern Analysis and Machine Intelligence; 12(7)629-639.

Rudin, L. I., et al.; Nonlinear total variation based noise removal algorithms; 1992; Physics; D 60:259-268.

Santamaria-Pang, A., et al.; Automated liver lesion characterization using fast kVp switching dual energy computed tomography imaging; 2010; Proc. SPIE Medical Imaging-Computer-Aided Diagnosis; 76240V; abstract.

Szczykutowicz, T. P., et al.; The dependence of image quality on the number of high and low kVp projections in dual energy CT using the Prior Image Constrained Compressed Sensing (PICCS) algorithm; 2010; Proc. SPIE Medical Imaging-Physics of Medical Imaging; pp. 762221-76221-10.

Thevenaz, P., et al.; Interpolation Revisited; 2000; IEEE Trans. on Medical Imaging; 19(7)739-758.

Tomasi, C., et al., Bilateral Filtering for Gray and Color Images; 1998; Proc. of the 1998 IEEE Int'l Conf. on Computer Vision; Bombay, India.

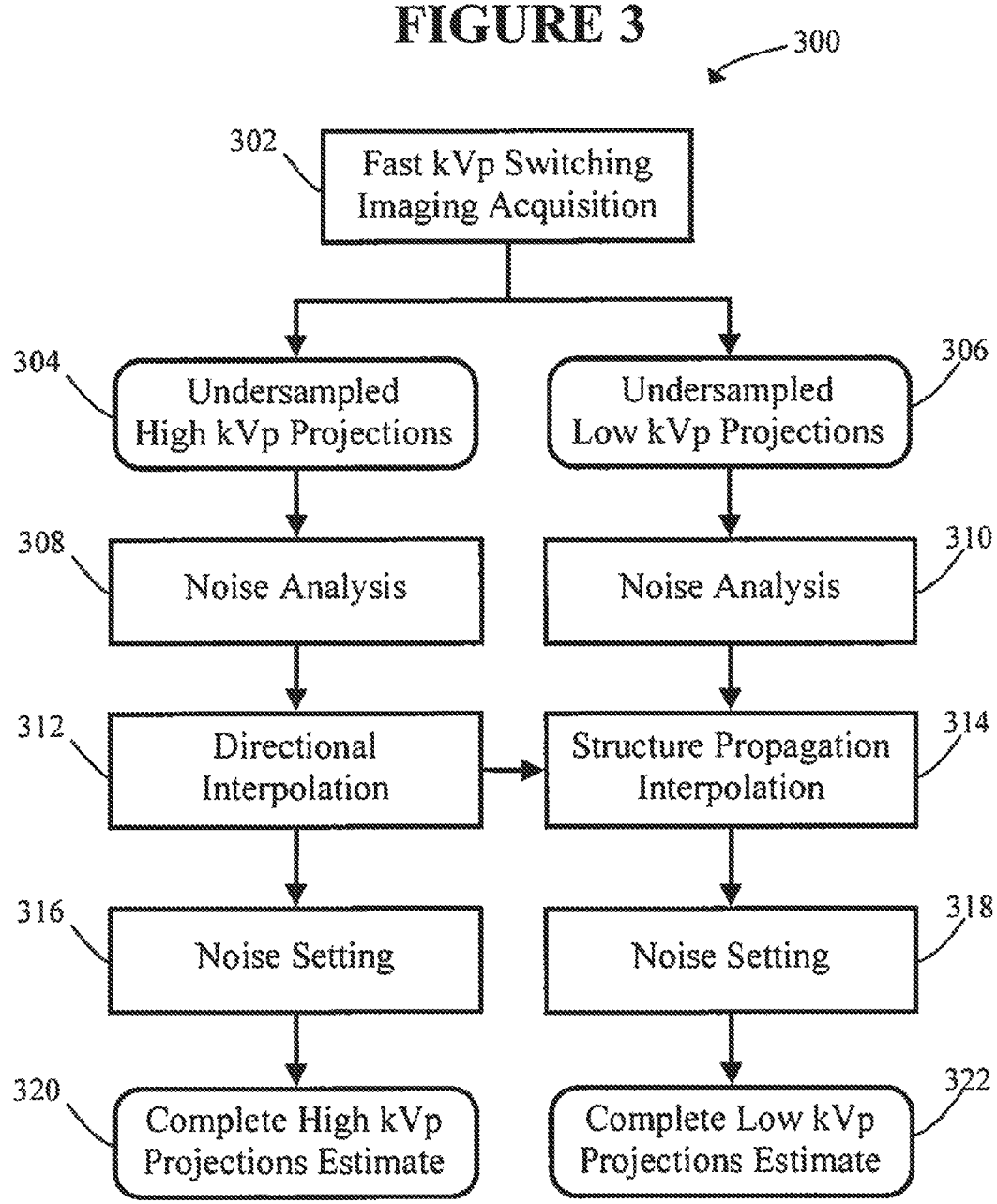

METHOD AND SYSTEM FOR DUAL ENERGY CT IMAGE RECONSTRUCTION

CROSS REFERENCE TO RELATED APPLICATIONS

This application is a national filing of PCT application Serial No. PCT/IB2012/050234, filed Jan. 18, 2012, published as WO 2012/104740 Al on Aug. 9, 2012, which claims the benefit of U.S. provisional application serial no 61/438, 344filed Feb. 1, 2011, which is incorporated herein by reference.

The present application relates generally to the imaging arts and more particularly to a method and system for reconstructing dual-energy or other multi-energy computed tomography (CT) imaging data. The application subject matter finds particular use in connection with medical imaging systems. However, in its broader aspects, the application subject matter is not limited to the medical imaging field, and may apply in other fields such as for example imaging for security purposes in airports or other checkpoints.

Spectral CT, and in particular fast kVp (kilovoltage peak) switching dual-energy CT, is an imaging modality that can extend the capabilities of single-energy CT in some circumstances. As one example, two different materials being imaged may attenuate a single-energy x-ray beam in approximately the same manner, making it difficult to differentiate between the two materials with the single-energy x-ray beam. If two or more x-ray beams are instead employed, with each beam having a different energy than the other beam(s), the additional information provided by the differing energy x-ray beams may be used to more easily differentiate between the two materials. Thus dual-energy CT techniques utilize two x-ray attenuation values acquired at two x-ray photon energies to solve the photoelectric and Compton contribution resulting from the mass attenuation coefficient of a material, and thus to identify an unknown material by its value of photoelectric and Compton contribution. This scheme works especially well in materials such as iodine having a k-edge energy close to the mean value of a diagnostic energy range. Because any two linearly independent sums of two basis functions span the entire attenuation coefficient space, any material can be represented by a linear combination of two other materials, so-called basis materials, such as water and iodine. The basis material images provide new applications such as generating a monochromatic image, a material cancellation image, an effective atomic number image or an electron density image.

In a typical CT acquisition, the x-ray source and the x-ray detector are rotated together on a common gantry support around the object to be imaged. The source and detector are disposed on opposite sides of the imaged object, so that x-rays emitted by the x-ray source are attenuated as they pass through the imaged object to be detected by the x-ray detector. The signals of the attenuated x-rays as recorded by the detector at various view angles during the rotation, called projections, may then be processed using known reconstruction techniques to generate an image of the object. In some alternative arrangements, only the x-ray source rotates while a series of stationary x-ray detectors disposed in a complete or partial ring around the imaged object record the projection data.

Performing dual-energy CT imaging scans requires an x-ray source or sources which provide x-ray beams at two energies, as well as an x-ray detector or detectors which can record the differing energy x-ray beams after they pass through the imaged object. Recent technical advances have provided several designs for such source(s) and such detector (s). In one conventional approach, a fast kVp switching x-ray source is provided. In this approach, the voltage and perhaps also the current supplied to the x-ray source are varied in a controlled manner to provide a high energy x-ray beam and a low energy x-ray beam in alternating fashion between projections. The detector, in turn, is configured to detect both the high energy x-rays and the low energy x-rays, such as for example with two stacked layers of detector elements each respectively suited to detect the higher or lower energy x-rays. Use of a fast kVp switching x-ray source allows for good temporal resolution as the spectral data is being acquired in an alternating manner between projections.

This conventional dual-energy CT scanning with fast kVp switching is schematically illustrated in FIG. 2. In that illustration, the horizontal axis plots the projection angles as the x-ray source and the x-ray detector rotate around the imaged object, while the vertical axis plots the energy of the x-ray beam at each projection angle. Each bar represents a projection angle at which x-rays are generated and x-ray data is recorded. As can be seen, the x-ray source alternates between producing low energy $E_l$ and high energy $E_h$ x-ray beams. However, in this conventional method, the intensity of the beams remains a constant $I_0$. The gaps between the bars illustrate that it takes some amount of time for the energy of the x-ray beam to switch from the low level to the high level, and from the high level back to the low level. Thus, for some intermediate projection angles, no data is recorded as the x-ray source is being switched and rotated at the same time.

One potential difficulty with fast kVp switching CT scans is that a conventional reconstruction of the respective low energy and high energy data sets results in low quality images. That is, there is not enough low energy data to generate an image of sufficient quality from the low energy data alone, and there is not enough high energy data to generate an image of sufficient quality from the high energy data alone. By dividing the projection angles into low energy projections and high energy projections, both the low energy and high energy projection data sets are undersampled.

In accordance with aspects of the present invention, a method and system for dual energy CT image reconstruction are provided. In one aspect, a fast kVp switching x-ray source is used during an imaging scan to alternately produce a low energy x-ray beam for L consecutive projection angles and a high energy x-ray beam for H consecutive projection angles, wherein L is substantially less than H. Methods are provided for estimating the resulting undersampled data in the low energy projection data set and the high energy projection data set. The missing low energy projection data may be estimated from the known high energy projection data using any one of several disclosed structural propagation embodiments.

Numerous advantages and benefits will become apparent to those of ordinary skill in the art upon reading the following detailed description of the preferred embodiments. The invention may take form in various components and arrangements of components, and in various process operations and arrangements of process operations. The drawings are only for the purpose of illustrating preferred embodiments and are not to be construed as limiting the invention.

FIG. 3 illustrates a process for reconstructing dual-energy CT data;

Figure 1:
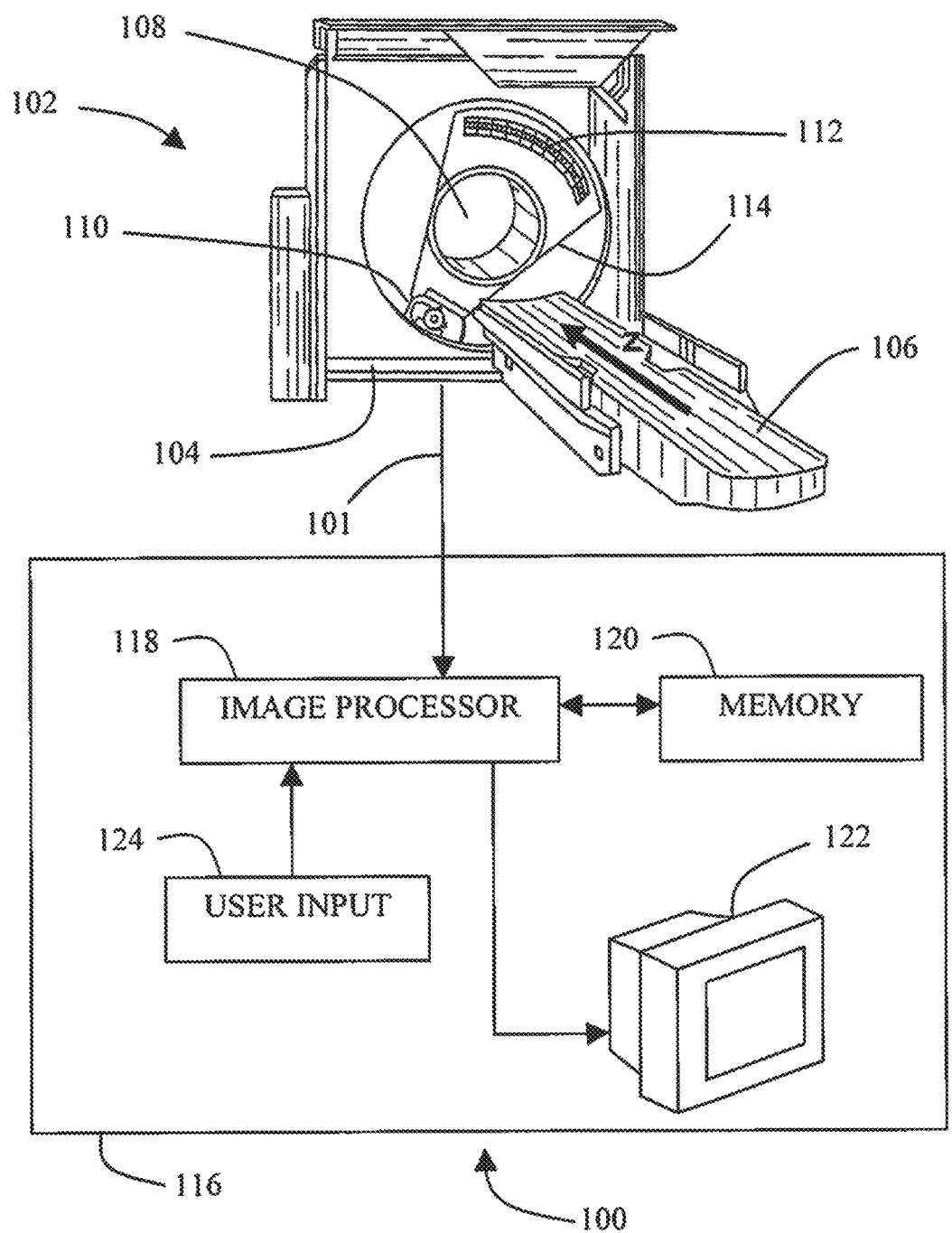
FIG. 1 is an exemplary CT imaging system, with a portion of the stationary gantry cut away to reveal the rotating x-ray source and data measurement system within the gantry.

The subject matter of the present disclosure finds use in connection with any dual-energy imaging system, for example, a dual-energy CT imaging system. More specifically, with reference to FIG. 1, in an exemplary embodiment the imaging system 100 is a medical CT imaging system. A CT imaging acquisition system 102 includes a gantry 104 and an object support 106 such as a table or couch which moves along the z-axis. A patient or other object to be imaged (not shown) lies or is placed down on the object support 106 and is moved to be disposed within an aperture 108 in the gantry 104. Once the patient or object is in position within the aperture 108, an x-ray source 110 emits a projection of x-rays to be gathered by an x-ray data measurement system 112 inside the gantry 104. (A portion 114 of the gantry 104 is cut away in FIG. 1 to show the x-ray source 110 and x-ray data measurement system 112 which are housed inside the gantry 104.) The x-ray source 110 may emit x-rays having at least two different energy levels, and the x-ray data measurement system 112 may detect x-rays having those different energy levels. The x-ray source 110 and data measurement system 112 rotate together around the aperture 108 to record CT imaging data from various positions, or projections. In some embodiments such rotation may occur while the object support 106 is stationary. In other embodiments such rotation may occur in conjunction with linear movement of the object support 106 along the z-axis in a "helical" scan. The rotation is possible because the x-ray source 110 and the data measurement system 112 are each mounted to a common rotor (not shown) inside the gantry 104.

The data measurement system 112 of the CT imaging acquisition system 102 thus acquires CT imaging data in the form of detected x-rays. The system 102 then transfers the acquired CT imaging data on to a CT imaging, processing and display system 116 through a communication link 101. Although the systems 102 and 116 are shown and described here as being separate systems for purposes of illustration, they may in other embodiments be part of a single system. When the systems 102 and 116 are separate systems, the communication link 101 may be any link which permits the transfer of data between the systems, such as a Local Area Network, the Internet, a physical transfer of a memory storage medium such as a computer diskette, CD-ROM, or flash drive, or the like. The communication link 101 may be wired, wireless, or a combination thereof. Thus, the systems 102 and 116 may be located in different rooms, different buildings, or even different cities.

Via the communication link 101, the acquired CT imaging data passes to an image processor 118 which stores the acquired CT imaging data in a memory 120. The image processor 118 applies image reconstruction techniques to electronically process the acquired CT imaging data and generate reconstructed imaging data, comprising images of the imaged patient or other object. The image processor 118 can show the resulting reconstructed imaging data on an associated display 122. A user input 124 such as a keyboard and/or mouse device may be provided for a user to control the processor 122.

The imaging system 100 may be a stand-alone unit which provides only CT-based imaging, as is shown in FIG. 1.

Although not shown here, the imaging system 100 may additionally include appropriate components for PET and/or SPECT imaging, or some other imaging modality, in conjunction with the CT-based imaging components.

Thus the functions described herein can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as memory 120, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the memory 120. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Figure 2:
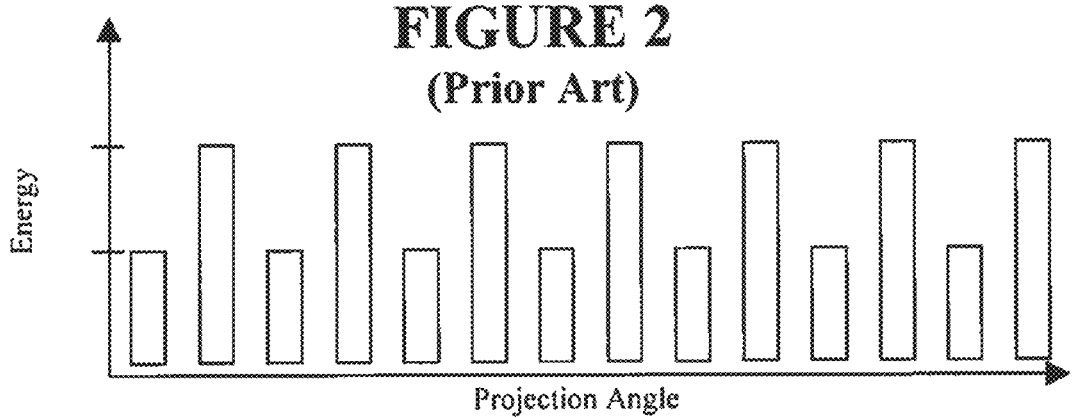
FIG. 2 is a schematic illustration of a conventional fast kVp switching CT scan.
Figure 4:
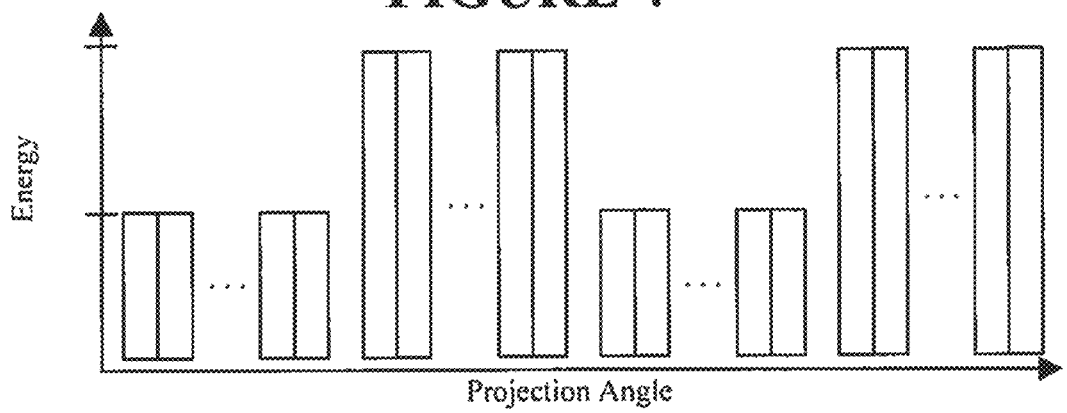
FIG. 4 is a schematic illustration of a fast kVp switching CT scan useful for reconstructing dual-energy CT imaging data.

The present disclosure provides a method and system for reconstructing dual-energy computed tomography (CT) imaging data. An exemplary method process 300 is illustrated in FIG. 3. In a first step 302, a fast kVp switching imaging acquisition is performed. The fast kVp switching imaging acquisition 302 results in two data sets: an undersampled high energy projection data set 304 and an undersampled low energy projection data set 306. More specifically, during the acquisition L consecutive projection angles are recorded at a low x-ray energy, and then H consecutive projection angles are recorded at a high x-ray energy, in an alternating manner. L is substantially less than H. This is schematically illustrated in FIG. 4. In that illustration, the horizontal axis plots the projection angles as the x-ray source and the x-ray detector rotate around the imaged object, while the vertical axis plots the energy of the x-ray beam at each projection angle. Each bar represents a projection angle at which x-rays are generated and x-ray data is recorded. As can be seen, the x-ray source alternates between producing a low energy x-ray beam $E_l$ for l=1, 2, . . . , L consecutive projection angles, and then producing a high energy x-ray beam $E_h$ for h=1, 2, . . . , H projection angles. The gaps between the final bar at one energy level, and the first bar at the next energy level, illustrate that it takes some amount of time for the energy of the x-ray beam to switch from the low level to the high level, and from the high level back to the low level. Thus, for some intermediate projection angles, no data is recorded as the x-ray source is being switched and rotated at the same time. The lack of gaps between adjacent bars at the same energy level illustrates that no delay is required between such measurements, because the energy of the x-ray beams remains constant. In the terms of this framework, it can be seen that the prior art acquisition mode illustrated in FIG. 2 represents the case where L=H=1.

Figure 5:
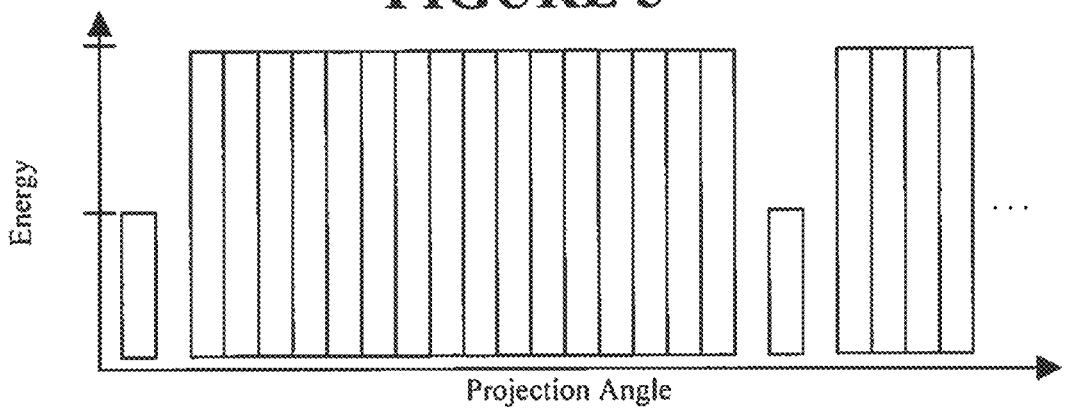
FIG. 5 is a schematic illustration of the CT scan from FIG. 4 when L=1 and H=16.

The ratio L:H is preferably substantially less than 1. In various embodiments, L/H may be no more than about 0.50, no more than about 0.25, no more than about 0.10, no more than about 0.06, no more than about 0.05, or no more than about 0.04. In a most preferred embodiment of the present disclosure, L=1 but H is substantially greater than 1, such as for example H is equal to at least 5, or H is equal to at least 10, or H is equal to at least 15, or H is equal to at least 20, or H is equal to at least 25. FIG. 5 illustrates the specific example where L=1 and H=16. As will be appreciated by one of ordinary skill, choosing appropriate values for L and for H will depend on various scan parameters of the particular apparatus and scan methodology being utilized. Such scan parameters include, for example, scan type, current and voltage capabilities of the x-ray source (mA and kVp), pitch, rotation time, reconstruction or convolution filter, what object(s) are being imaged, and the like.

When the ratio L:H is substantially less than 1, the fundamental problem of angular undersampling of low and high energy projections still exists. The low energy projections are very sparse while the high energy projections are often not entirely complete, although the latter may be almost complete.

In the context of the present application, "low" energy and "high" energy are relative not absolute descriptors. That is, the "low" energy level $E_l$ is less than the "high" energy level $E_h$, and the "high" energy level $E_h$ is greater than the "low" energy level $E_l$. These two energy levels $E_l$, $E_h$ are not necessarily lower or higher than any other benchmark values. In addition, one of ordinary skill will appreciate that any given x-ray beam will typically be comprised of x-ray photons having a distribution of energies; they will not all have the exact same energy. Thus, a reference to the energy of an x-ray beam refers to some characteristic of the energy distribution in the x-ray beam, such as the most prominent energy, the mean energy, the highest energy, or the like.

As already discussed, the energy E of the x-ray beam is varied by modulating the voltage (kVp) supplied to the x-ray source. Fast kVp switching as described herein can, however, disadvantageously cause difficulties in matching the noise characteristics between the low energy and high energy spectral CT data. That is because many currently available CT systems cannot modulate the x-ray source current (mA) at the same rate as the x-ray source voltage (kVp). The x-ray source current determines the intensity of the x-ray beam. Despite these hardware difficulties, in some embodiments it may be useful to modulate the x-ray source voltage (i.e. beam energy) and current (i.e. beam intensity) at the same time.

For example, in many instances, the low energy projection data 306 is much more noisy than the high energy projection data 304. To help reduce the signal-to-noise ratio, the intensity of the low energy x-ray beams $I_l$ may be greater than the intensity of the high energy x-ray beams $I_h$. In other embodiments, the intensity of the low and high energy beams may be the same. In yet further embodiments, the intensity of the low energy x-ray beams may be less than the intensity of the high energy x-ray beams.

Returning to FIG. 3, in the next and optional steps 308 and 310, the data sets 304 and 306 are respectively analyzed to remove noise from the data. Because the projection data 304, 306 incorporates cumulative information of the imaged object structure, a high sensitivity to low contrast structures in the imaging data can be useful. Therefore, the low contrast clustering (LCC) algorithm of pending U.S. Provisional Patent Application Ser. No. 61/418,422, entitled Contrast to Noise Ratio (CNR) Enhancer and filed on Dec. 1, 2010, is an attractive option for performing the steps 308 and 310. That application is incorporated herein by reference for its disclosure of the LCC algorithm and other noise estimation techniques. Generally speaking, the LCC algorithm consists of three main steps: noise modeling, local structure estimation, and clustering. In the noise modeling step, the data 304, 306 is analyzed to estimate the data noise pattern. In the local structure estimation step, the data 304, 306 is processed to improve the local contrast to noise ratio throughout the data. In the clustering step, a final piece-wise smooth approximation of the data is performed. This LCC algorithm provides a high sensitivity to low contrast structures in the imaging data.

As alternatives to the LCC algorithm, any one of several well known edge preserving noise removal algorithms can be employed in step 308 and/or step 310. Such algorithms include bilateral filtering such as disclosed by C. Tomasi and R. Manduchi, "Bilateral Filtering for Gray and Color Images", Proceedings of the 1998 IEEE International Conference on Computer Vision; a diffusion filter such as disclosed by P. Perona and J. Malik, "Scale-Space and Edge Detection Using Anisotropic Diffusion", IEEE Transactions on Pattern Analysis and Machine Intelligence, vol. 12, no. 7 (1990), pp. 629-39; a total variation de-noising such as disclosed by L. Rudin, S. Osher and E. Fatemi, "Nonlinear Total Variation Based Noise Removal Algorithms", Physica D, vol. 60 (1992), pp. 259-268; or a mean-shift algorithm such as disclosed by D. Comaniciu and P. Meer, "Mean Shift: a Robust Approach Toward Feature Space Analysis", IEEE Transactions on Pattern Analysis and Machine Intelligence, vol. 24, no. 5 (2002), pp. 603-619. Each one of those publications is incorporated herein by reference for their respective disclosures concerning noise removal algorithms.

In the next step 312 of the process 300 as illustrated in FIG. 3, the missing data in the undersampled high kVp projection data set 304 is estimated. When L is substantially less than H, the high kVp projection data set 304 is almost complete. Indeed, if H is large enough, the estimation step 312 may be omitted. If estimation within the high kVp projection data set 304 is desirable or necessary, however, a conventional directional interpolation technique performs the estimation very well. Various alternative methods for linear or nonlinear interpolation of biomedical image data have been proposed in the literature. Such publications include T. Lehmann, C. Gonner, and K. Spitzer, "Survey: Interpolation Methods in Medical Image Processing", IEEE Transactions on Medical Imaging, vol. 18, no. 11 (1999), pp. 1049-1075; T. Lehmann, C. Gönner and K. Spitzer, "Addendum: B-Spline Interpolation in Medical Image Processing", IEEE Transactions on Medical Imaging, vol. 20, no. 7 (2001), pp. 660-665; P. Thévenaz, T. Blu, and M. Unser, "Interpolation Revisited", IEEE Transactions on Medical Imaging, vol. 19, no. 7 (2000), pp. 739-758; G. Grevera and J. Upuda, "An Objective Comparison of 3-D Image Interpolation Methods", IEEE Transactions on Medical Imaging, vol. 17, no. 4 (1998), pp. 642-652; J. Hladuvka and E. Gröller, "Direction-Driven Shape-Based Interpolation of Volume Data", Proceedings Vision, Modeling, and Visualization, Stuttgart, Germany (2001), pp. 113-120 and 521; and M. Bertram, G. Rose, D. Schäfer, J. Wiegert and T.

Aach, "Directional Interpolation of Sparsely Sampled Cone-Beam CT Sinogram Data", Proceedings IEEE International Symposium on Biomedical Imaging, Vienna, Austria (2004). Each one of those publications is incorporated herein by reference for their respective disclosures concerning data interpolation techniques.

One particularly attractive technique in the context of the present application is the Bertram et al. technique, in which the structure tensor is utilized to estimate the direction of gray value changes in local neighborhoods and then this information is utilized for directional interpolation. If the optional noise removal steps 308, 310 were performed, then the interpolation step 312 is performed on the high kVp projection data 304 with the noise removed from it. Regardless, the interpolation 312 results in an estimated, completely sampled high kVp projection data set.

In the next step 314 of the process 300 as illustrated in FIG. 3, the missing data in the undersampled low kVp projection data set 306 is estimated. When L is substantially less than H, the low kVp projection data set 306 is sparse. In a preferred embodiment, this estimation 314 is performed using a structure propagation interpolation technique, which propagates structural information of the high kVp data 304 to the low kVp data 306. There are at least three different methods for performing this step 314: a gradient direction preserving method, a local similarity transformation method, and a nearest neighbor method.

Concerning the gradient direction preserving method, the basic principle behind this method is that the structural information of the scanned object is captured by the gradients of the high kVp projection data 304. That is, the boundaries between different objects within the imaging data, such as different organs or tissues, are defined by the directions of the gradients. Therefore, the gradient direction preserving method estimates missing data in the low kVp projection data 306 under the constraints of having the gradient directions correspond to the gradient directions of the high kVp projection data 304. This principle can be approximated by minimization of the following expression:

$$\{\hat{L}(i, j)\} = \operatorname*{argmin}_{L(i,j) \in L_m} \sum_i \sum_j \left( \frac{\frac{\partial L}{\partial j}(i, j)}{\frac{\partial L}{\partial i}(i, j)} - \frac{\frac{\partial H}{\partial j}(i, j)}{\frac{\partial H}{\partial i}(i, j)} \right)^2 w(\|\nabla H(i, j)\|)^2, \quad \text{(Eq. 1)}$$

where L is a sinogram consisting of the low kVp projection data 306, H is the corresponding sinogram of the high kVp projection data 304, i is the index over the detector readings, j is the index over the projection angles, $L_m$ is the set of missing data samples in the low kVp projection data 306, and w is a weight function which is a monotonic increasing function.

However, the above minimization problem may be ill-conditioned or singular yielding a non-unique solution. In order to obtain robust solutions, a regularization function may be included in the minimization such as:

$$\{\hat{L}(i, j)\} = \operatorname*{argmin}_{L(i,j) \in L_m} \sum_i \sum_j \left( \begin{array}{l} \psi\left(\frac{\partial H}{\partial i}(i, j)\right)(L(i, j+1) - L(i, j-1)) - \\ \frac{\partial H}{\partial j}(i, j)(L(i+1, j) - L(i-1, j)) \end{array} \right)^2 \quad \text{(Eq. 2)}$$

$$\psi(w(\|\nabla H(i, j)\|))^2,$$

where $\Psi$ is a regularization function defined as follows:

$$\psi(x) = \begin{cases} x, & |x| > \varepsilon \\ \varepsilon, & \text{otherwise,} \end{cases} \quad \text{(Eq. 3)}$$

and where $\epsilon$ is a small number. The minimization problem of Equation 2 can be solved efficiently using the weighted linear least squares method.

Figure 6:
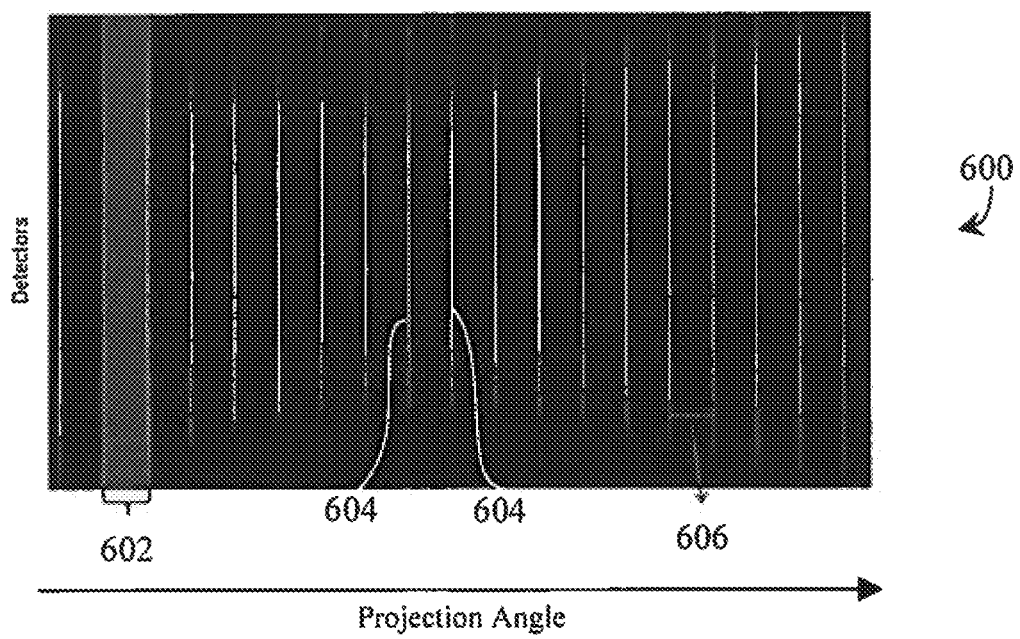
FIG. 6 is a representative sinogram of a low kVp projection data set when L=1 and H=16.

In the minimization expression of Equation 2, the central difference finite approximation is used to approximate the derivatives in Equation 1. However, forward and backward difference finite approximations can be utilized as well, in order to allow segment by segment sinogram processing. In this context, a sinogram segment is defined as the "missing" low kVp projection data between two adjacent low kVp projection data measurements. A sinogram segment is shown, for example, in FIG. 6 at 602. That figure shows a representative sinogram 600 of a low kVp projection data set 306 taken with L=1 and H=16. The horizontal axis plots the projection angles, and the vertical axis plots the data recorded by the detectors at each angle. Thus, each vertical line 604 of data in FIG. 6 corresponds to one of the low kVp projection angles. The space between the vertical lines corresponds to the 16 interleaving high kVp projections, plus one projection at each transition between low and high energies, for a total of 18 projection angles making up each sinogram segment.

Turning now to the local similarity transformation method, the underlying assumption behind this method is that the missing data in the low kVp projection data set 306 can be locally approximated by a similarity transformation of the high kVp projection data set 304. The local similarity transformation is estimated for each of the line segments in the low kVp projection sinogram, where a line segment is a row segment in the sinogram section between two adjacent low kVp projection data measurements. This is shown, for example, in FIG. 6 at 606. In most instances, a local similarity transformation is less accurate than the gradient direction preserving method, but it is also simpler and faster.

In one application of the local similarity transformation method, let $L^i$ be the i-th line segment of length H+4 in a low kVp projection data set 306 sinogram that was acquired with an L=1 dual kVp scheme. Note that all the entries except the first and the last entries of E are empty (missing readings). Let $H^1$ be the corresponding line segment in the high kVp projection data set 304 sinogram. The local similarity transformation in this case can be defined by two parameters: a scale parameter $\alpha$ and a translation parameter t. The two parameters are estimated as follows:

$$\alpha^i = \frac{\vec{L}_1^i - \vec{L}_{n+4}^i}{\vec{H}_1^i - \vec{H}_{n+4}^i} \quad \text{(Eqs. 4 and 5)}$$

$$t^i = \vec{L}_1^i(\vec{H}_{n+4}^i - \vec{H}_1^i) + \vec{H}_1^i(\vec{L}_{n+4}^i - \vec{L}_1^i),$$

Once the transformation parameters are estimated, the missing readings of the low kVp projection data set 306 are estimated as follows:

$$\vec{L}^i = \alpha^i \vec{H}^i + t^i \qquad \text{(Eq. 6)}$$

This method can be applied robustly and very efficiently over the whole sinogram, since the transformation parameters are estimated using a closed-form expression.

Figure 7:
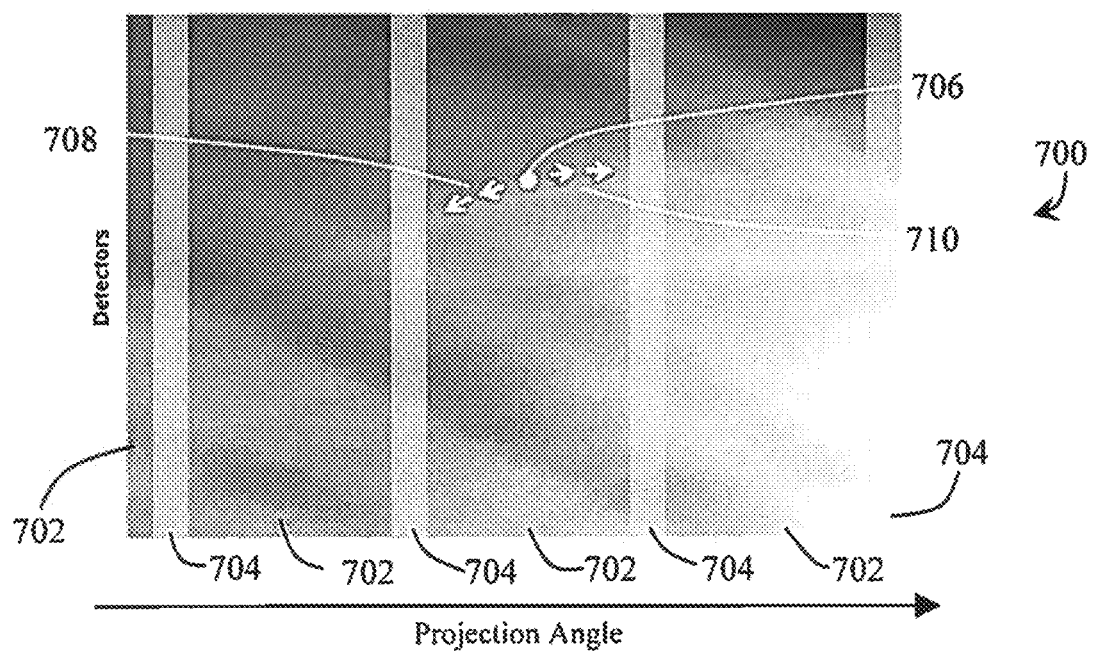
FIG. 7 is a portion of a representative sinogram of a high kVp projection data set when L=1 and H=16.

Turning now to the nearest neighbor method, the underlying assumption behind this method is that the missing data in the low kVp projection data set 306 can be locally approximated by a translation transformation of the high kVp projection data set 304. In this method the local translation transformation is estimated for each data point in the low kVp sinogram using a nearest neighbor like approach. For each missing data point in the low kVp projection data 306, optimal trajectories are estimated over the high kVp sinogram. For example, FIG. 7 illustrates a portion 700 of a representative sinogram of a high kVp projection data set 304 when L=1 and H=16. Thus, the areas 702 correspond to portions of the high kVp data 304, whereas the other areas 704 correspond to portions of the low kVp projection data 306. In other words, in the corresponding low kVp projection sinogram (not shown), areas 702 are missing data points while areas 704 contain data points. So, for example, point 706 is lacking low kVp data, which therefore needs to be estimated for point 706. Trajectories 708, 710 start at the current data point 706 and end in two non-missing low kVp data points, in the adjacent regions 704 corresponding to two different projection angles. The optimal trajectories are estimated using a fast-marching algorithm. The energy function of the fast-marching algorithm depends on the similarity of the points throughout the trajectory to the current missing data point and also depends on the curvature of the trajectory. Once the trajectories are estimated, the two end points of the trajectories are utilized to estimate two translation transformations from the high kVp data 304 to the low kVp data 306. The two transformations are used to estimate two estimates for the low kVp missing data point. The final estimate is calculated using a weighted average of the two estimates, where the weight of each estimate is the value of the cost of the trajectory to the other end point.

In one application of the nearest neighbor method, let C(•) be a cost function that depends on the similarity of the neighborhood of two data points and on the local curvature of the trajectory. Then, for each missing data point p in the low kVp projection data set 306, perform an estimate as follows. Using a fast-marching algorithm and the cost function C(•), estimate optimal trajectories $T^+$ and $T^+$ in the high kVp projection data set 304 sinogram from the entry corresponding to the data point p to entries that correspond to two non-missing low kVp data points of two different projection angles. Estimate the missing data point value using translation transformations as follows:

$$\hat{L}(p) = \frac{(H(p) + L(T^+_{end}) - H(T^+_{end}))C(T^-) + (H(p) + L(T^-_{end}) - H(T^-_{end}))C(T^+)}{C(T^-) + C(T^+)}, \qquad \text{(Eq. 7)}$$

where $T_{end}^+$ and $T_{end}^-$ are the end points of the trajectories $T^+$ and $T^-$ respectively.

In the next steps 316 and 318 of the algorithm 300 as illustrated in FIG. 3, the noise is injected back into the data 304 and 306 (assuming optional steps 308 and 310 were employed). Where L: H is substantially less than 1, the high kVp projection data set 304 is almost complete. Therefore, for the high kVp projections, the noise may be simply added back to the data in step 316. For the low kVp projection data set 306, where the projections are very sparse, the noise estimate is also very sparse. So, the noise estimate from the high kVp projection data may be added to the low kVp projection data. However, matching the noise between the low and high energy spectral data may be difficult due to the limitations of current CT systems, which cannot modulate the x-ray source current (mA) at the same rate as the x-ray source voltage (kVp). In order to overcome this difficulty, the high kVp noise estimate may be multiplied by a compensation factor, which is set to compensate for the differences between the noise levels. The noise compensation factor can depend on, for example, the x-ray tube spectrum, the system filters, the scanned object, and the spectrum absorption profile of each of the spectral energy bins. After the multiplication, the noise from the high kVp projection data may be added to the low kVp projection data to generate the final estimate in step 318.

Once all the missing data is estimated, the result of the process 300 is an estimated complete high kVp projection data set 320 and an estimated complete low kVp projection data set 322. These data sets 320, 322 can be utilized within the wide spectrum of available dual energy CT applications. Such applications include, for example, filtered back projection reconstruction of high and low energy images, material separation, monochromatic image reconstruction, basis material image reconstruction, bone removal, iodine maps, virtual noncontrast images (VNC), dual energy electronic cleansing, lesion characterization, and other applications. One benefit achieved by the processes disclosed herein is that the complete estimated data sets 320, 322 are determined without the need to reconstruct the undersampled data sets 304, 306 or perform any other image reconstruction.

The invention has been described with reference to the preferred embodiments. Obviously, modifications and alterations will occur to others upon reading and understanding the preceding detailed description. For example, although the above-described preferred embodiment is a dual-energy spectral CT application, the concept applies equally well to higher order spectral CT. That is, it applies to tri-energy, quad-energy, and other contexts where more than two energy levels are involved. For example, there may be one high energy level but two different low energy levels to increase the sensitivity of the system.

It is intended that the invention be construed as including all such modifications and alterations insofar as they come within the scope of the appended claims or the equivalents thereof The invention may take form in various compositions, components and arrangements, combinations and sub-combinations of the elements of the disclosed embodiments.

The invention claimed is:

1. A method for dual energy CT image reconstruction, the method comprising:
performing an imaging scan in which L consecutive projection angles are measured at a low x-ray energy, and H consecutive projection angles are measured at a high x-ray energy, in an alternating manner, wherein L is substantially less than H, to generate a low energy projection data set comprising the projection angle measurements at the low energy and a high energy projection data set comprising the projection angle measurements at the high energy;
estimating an undersampled portion of the low energy projection data set to produce an estimated complete low energy projection data set, wherein the low energy estimation is performed without an image reconstruction of the low energy projection data set or the high energy projection data set; and removing noise from the low energy projection data set, then estimating the undersampled portion to generate the estimated complete low energy projection data set, and then injecting noise into the estimated complete low energy projection data set.

2. The method of claim 1, wherein low energy x-rays and high energy x-rays are alternately produced with a fast kVp switching x-ray source.

3. The method of claim 1, wherein the noise removal is performed using any one or more of a low contrast clustering algorithm, a bilateral filtering, a diffusion filter, a total variation de-noising, and a mean-shift algorithm.

4. The method of claim 1, wherein the noise injection comprises multiplying a high energy projection noise by a compensation factor in order to estimate a low energy projection noise.

5. The method of claim 1, wherein estimating the undersampled portion of the low energy projection data set comprises a structure propagation interpolation based on the high energy projection data set.

6. The method of claim 5, wherein the structure propagation interpolation comprises any one or more of a gradient direction preservation, a local similarity transformation, and a nearest neighbor calculation.

7. The method of claim 1 wherein L/H is equal to no more than about 0.5.

8. The method of claim 7, wherein a voltage supplied to an x-ray source is varied to produce low energy x-rays and high energy x-rays, and the method further comprises varying a current supplied to the x-ray source so that the intensity of the low energy x-rays is greater than the intensity of the high energy x-rays.

9. The method of claim 1, further comprising estimating an undersampled portion of the high energy projection data set to produce an estimated complete high energy projection data set, wherein the high energy estimation is performed without an image reconstruction of the low energy projection data set or the high energy projection data set.

10. The method of claim 9, wherein estimating the undersampled portion of the high energy projection data set comprises directional interpolation.

11. The method of claim 1, wherein no estimation of an undersampled portion of the high energy projection data set is performed.

12. A system for dual energy CT image reconstruction, the system comprising software embodied on a non-transitory tangible medium and readable by a computer, the software comprising logic to:

receive and store in a memory a dual energy CT imaging data acquired during an imaging scan in which L consecutive projection angles are measured at a low x-ray energy, and H consecutive projection angles are measured at a high x-ray energy, in an alternating manner, wherein L is substantially less than H, to generate a low energy projection data set comprising the projection angle measurements at the low energy and a high energy projection data set comprising the projection angle measurements at the high energy; and estimate an undersampled portion of the low energy projection data set to produce an estimated complete low energy projection data set, wherein the low energy estimation is performed without an image reconstruction of the low energy projection data set or the high energy projection data set; and remove noise from the low energy projection data set, then estimate the undersampled portion to generate the estimated complete low energy projection data set, and then inject noise into the estimated complete low energy projection data set.

13. The system of claim 12, wherein the imaging scan is performed using a fast kVp switching x-ray source to alternately produce low energy x-rays and high energy x-rays.

14. The system of claim 12, further comprising logic to perform the noise removal using any one or more of a low contrast clustering algorithm, a bilateral filtering, a diffusion filter, a total variation de-noising, and a mean-shift algorithm.

15. The system of claim 12, further comprising logic to perform the noise injection by multiplying a high energy projection noise by a compensation factor in order to estimate a low energy projection noise.

16. The system of claim 12, further comprising logic to estimate the undersampled portion of the low energy projection data set using a structure propagation interpolation based on the high energy projection data set.

17. The system of claim 16, wherein the structure propagation interpolation comprises any one or more of a gradient direction preservation, a local similarity transformation, and a nearest neighbor calculation.

18. The system of claim 12 wherein L/H is equal to no more than about 0.5.

19. The system of claim 18, wherein the imaging scan is performed by varying a voltage supplied to an x-ray source to produce low energy x-rays and high energy x-rays, and varying a current supplied to the x-ray source so that the intensity of the low energy x-rays is greater than the intensity of the high energy x-rays.

20. The system of claim 12, wherein the software further comprises logic to estimate an undersampled portion of the high energy projection data set to produce an estimated complete high energy projection data set, wherein the high energy estimation is performed without an image reconstruction of the low energy projection data set or the high energy projection data set.

21. The system of claim 20, wherein estimating the undersampled portion of the high energy projection data set comprises directional interpolation.

22. The system of claim 12, wherein no estimation of an undersampled portion of the high energy projection data set is performed.

23. A system for CT image reconstruction, the system comprising software embodied on a non-transitory tangible medium and readable by a computer, the software comprising logic to:

receive and store in a memory a CT imaging data acquired during an imaging scan in which L projection angles are measured at one or more low x-ray energies, and H projection angles are measured at one or more high x-ray energies, wherein each low x-ray energy is less than each high x-ray energy, and wherein L is substantially less than H, to generate a low energy projection data set comprising the projection angle measurements at the one or more low energies and a high energy projection data set comprising the projection angle measurements at the one or more high energies; and estimate an undersampled portion of the low energy projection data set to produce an estimated complete low energy projection data set, wherein the low energy estimation is performed without an image reconstruction of the low energy projection data set or the high energy projection data set; and remove noise from the low energy projection data set, then estimate the undersampled portion to generate the estimated complete low energy projection data set, and then inject noise into the estimated complete low energy projection data set.

24. The system of claim 23, further comprising two different low x-ray energies, and two different high x-ray energies.

25. The system of claim 23, wherein the software further comprises logic to estimate an undersampled portion of the high energy projection data set to produce an estimated complete high energy projection data set, wherein the high energy estimation is performed without an image reconstruction of the low energy projection data set or the high energy projection data set.

* * * * *